US012758161B2

(12) United States Patent
Kreher et al.

(10) Patent No.: US 12,758,161 B2
(45) Date of Patent: Oct. 13, 2026

(54) COMPUTER-IMPLEMENTED METHOD FOR ASCERTAINING AN ITEM OF TORSION INFORMATION OF A BONE, X-RAY FACILITY, COMPUTER PROGRAM AND ELECTRONICALLY READABLE DATA CARRIER

(71) Applicant: Siemens Healthcare GmbH, Erlangen (DE)

(72) Inventors: Björn Kreher, Bräuningshof (DE); Benedict Swartman, Mannheim (DE); Gerhard Kleinszig, Forchheim (DE); Alexander Gemmel, Erlangen (DE); Holger Kunze, Bubenreuth (DE); Markus Weiten, Nuremberg (DE); Jessica Magaraggia, Erlangen (DE); Maxim Fikuart, Mannheim (DE)

(73) Assignee: Siemens Healthineers AG, Forchheim (DE)

( * ) Notice: Subject to any disclaimer, the term of this patent is extended or adjusted under 35 U.S.C. 154(b) by 448 days.

(21) Appl. No.: 18/231,947

(22) Filed: Aug. 9, 2023

(65) Prior Publication Data

US 2024/0050045 A1 Feb. 15, 2024

(30) Foreign Application Priority Data

Aug. 10, 2022 (DE) ..................... 10 2022 208 323.7

(51) Int. Cl.
*A61B 6/00* (2024.01)
*A61B 6/02* (2006.01)
*A61B 6/50* (2024.01)

(52) U.S. Cl.
CPC ............ *A61B 6/025* (2013.01); *A61B 6/4441* (2013.01); *A61B 6/505* (2013.01); *A61B 6/5217* (2013.01); *A61B 6/5229* (2013.01)

(58) Field of Classification Search
CPC ...................................................... A61B 6/505
See application file for complete search history.

(56) References Cited

U.S. PATENT DOCUMENTS

2007/0161929 A1* 7/2007 Maier .................. A61B 5/4504 600/587
2016/0213343 A1* 7/2016 Barth ..................... A61B 6/505
2019/0117180 A1 4/2019 Gemmel et al.

FOREIGN PATENT DOCUMENTS

DE 102015201067 A1 7/2016

OTHER PUBLICATIONS

H.-A. Waidelich et al. "Computer tomography measurements of torsional angle and length in the lower extremitiesMethods, normal values and radiation dose" 157, 3. 1992, with Translation. pp. 1-16.

* cited by examiner

*Primary Examiner* — Dani Fox
(74) *Attorney, Agent, or Firm* — Lempia Summerfield Katz LLC

(57) ABSTRACT

Systems and methods for ascertaining an item of torsion information of a bone of a patient, wherein an X-ray facility with adjustable projection geometry of a recording arrangement described by projection parameters is used. A first X-ray image is recorded of an end region of the bone in a first projection geometry in which a torsion direction defined relative to at least one torsion landmark and used for ascertaining a roll angle lies in a first computing plane, which is formed by the focal point of the X-ray source and a reference direction which may be determined in the first X-ray image by at least one reference landmark. A second X-ray image is recorded of the end region of the bone in a second projection geometry with a direction of projection deviating from the direction of projection of the first projection geometry, and forming a second computing plane
(Continued)

from the reference direction which may be determined in the second X-ray image likewise by the at least one reference landmark, and the focal point. The three-dimensional course of the reference direction and the torsion direction is determined from the computing planes and the roll angle as the rotation of the torsion direction about the reference direction with respect to a comparison specification. The item of torsion information is ascertained from the roll angle.

20 Claims, 5 Drawing Sheets

COMPUTER-IMPLEMENTED METHOD FOR ASCERTAINING AN ITEM OF TORSION INFORMATION OF A BONE, X-RAY FACILITY, COMPUTER PROGRAM AND ELECTRONICALLY READABLE DATA CARRIER

CROSS REFERENCE TO RELATED APPLICATIONS

This application claims the benefit of DE 102022208323.7 filed on Aug. 10, 2022, which is hereby incorporated by reference in its entirety.

FIELD

Embodiments relate to a computer-implemented method for ascertaining an item of torsion information of a bone, for example the femur, of a patient. An X-ray facility with adjustable projection geometry of a recording arrangement described by projection parameters is used, which facility includes an X-ray source and an X-ray detector. In addition, embodiments relate to an X-ray facility, a computer program, and an electronically readable data carrier.

BACKGROUND

For bones, for example bones of the extremities, of the human body, different items of torsion information describing the orientation and also relative orientation of portions of bone are known, which are defined, for example, on the basis of suitable anatomical landmarks of the corresponding bone. In medicine, the torsion denotes the rotation of an anatomical feature about its own longitudinal axis, so items of torsion information contain indications about a possible incorrect orientation of bone parts interacting with other parts of the body.

Such considerations acquire particular relevance in the case of the human thigh bone, e.g., the femur. For example, a break to the femoral shaft occurs relatively frequently, with this fracture customarily being surgically stabilized by the introduction of a femoral nail. It is extremely important in this case that what is known as the antetorsion angle between the femoral neck shaft and the condyle plane is anatomically correctly established again before locking the femoral nail.

Methods have already been proposed in the prior art to quantify the antetorsion angle of a femur of a patient from three-dimensional computed tomography images, with, for example, the method according to Waidelich et al. being established in the meantime, cf. in this regard, for example, the article "Computertomographische Torsionswinkel-und Längenmessung an der unteren Extremität" [Computed tomography torsion angle and length measurement at the lower extremity] by H.-A. Waidelich et al., Fortschr. Röntgenstr. 157, 3 (1992), pages 245 to 251. Owing to the complex structure of the proximal femur, a computed tomography scan on both sides is required for determining the antetorsion, and this is customarily carried out after an operation since an intraoperative measurement with a computed tomography facility is not possible in many facilities.

If a patient has acute problems with their gait following an operation, the antetorsion angle is determined on both sides by a postoperative computed tomography scan. A revision operation is recommended when there is a difference between the right and left antetorsions of more than 12°. If the patient does not have any acute problems despite a misalignment, a revision operation is dispensed with in many cases, although this may still result in health limitations for the patient that last a relatively long time.

A computed tomography determination of the antetorsion angle intraoperatively may be carried out, for example when using an X-ray facility with a C-arm, in which by rotating the C-arm, on which an X-ray source and an X-ray detector are arranged facing each other, about the corresponding bone, different projection geometries may be adopted, which permit a three-dimensional computed tomography reconstruction. For example, a cone beam computed tomography scan may be carried out intraoperatively in the proximal end region and in the distal end region of the femur therefore to determine, proximally and distally respectively, the torsion of the joints in relation to the horizontal independently of each other. Torsion angle and direction angle respectively are determined on the basis of particular anatomical landmarks of the femur, it being possible to use, for example, proximally the femoral head and the trochanter major and the condyle plane being considered distally. The antetorsion angle is then given by the difference between the two torsions described by corresponding direction angles.

Such a method is not carried out in practice, however, since, firstly, X-ray facilities with isocentric C-arms suitable for three-dimensional imaging are too unwieldy for this type of operation. In addition, there is also the considerable amount of time required for carrying out two intraoperative three-dimensional computed tomography scans, so the total operation time would also be significantly lengthened.

It is therefore currently customary to reestablish the antetorsion without imaging before locking the femoral nail, for which purpose the positions of both legs and feet are aligned as symmetrically as possible. If the type of fracture allows, an attempt is also made to join the pieces of the fracture together again as exactly as possible on the edge of the break to thus reestablish the original antetorsion. These methods are characterized by rather high inaccuracy, however, so, for example, deviations of the antetorsion angle, misalignments therefore, of 150 or more may occur.

BRIEF SUMMARY AND DESCRIPTION

The scope of the present disclosure is defined solely by the claims and is not affected to any degree by the statements within this summary. The present embodiments may obviate one or more of the drawbacks or limitations in the related art.

Embodiments provide for determining items of torsion information of bone by way of X-ray imaging that is simple and time-efficient to implement.

A method includes the following steps: a) recording a first X-ray image of an end region of the bone in a first projection geometry in which a torsion direction defined relative to at least one torsion landmark and used for ascertaining a roll angle lies in a first computing plane, that is formed by the focal point of the X-ray source and a reference direction that may be determined in the first X-ray image by at least one reference landmark, for example parallel to the shaft axis of the bone; b) recording a second X-ray image of the end region of the bone in a second projection geometry with a direction of projection deviating from the direction of projection of the first projection geometry, for example at least substantially perpendicular to it, and forming a second computing plane from the reference direction that may be determined in the second X-ray image likewise by the at least one reference landmark, and the focal point; and c) ascertaining the three-dimensional course of the reference direction and the torsion direction from the computing planes and the roll angle as the rotation of the torsion direction about the reference direction with respect to a comparison specification, wherein the item of torsion information is ascertained from the roll angle.

A basic idea is to ascertain a relevant roll angle, for example in relation to the shaft direction of the shaft axis, using just two X-ray images. In this case it has been found that torsion directions, by which items of torsion information are defined, are customarily defined relative to at least one torsion landmark, with, for example, torsion directions that are used for defining angles, for example roll angles that describe the torsion, being considered. These torsion landmarks, that may include, for example, condyles, heads of bones, trochanters, and the like, may customarily be identified in X-ray images. Geometric conditions are established in which two X-ray images in different projection geometries, that use different directions of projection, are sufficient to easily determine roll angles as the basis of an item of torsion information. The roll angle customarily refers to a reference direction, that in most cases will be the medical definition of torsion following the shaft direction of the shaft axis. The torsion landmarks and thus the torsion directions may be defined if a bone is regarded in the longitudinal direction, in the direction of the shaft axis as the viewing direction therefore. While in many cases, for example in the case of antetorsion, difference angles, for example angles between torsion directions in the distal end region and torsion directions in the proximal end region therefore, are considered, applications may be provided where roll angles in only one end region in relation to a comparison specification are of interest, for example in the case of a follow-up during a procedure or the like.

The first projection geometry is selected such that it is possible not only to identify the reference direction on the basis of the reference landmarks, but instead the reference direction, together with the focal point of the X-ray source, then forms a first computing plane in which the torsion direction (and by definition, the reference direction) lie. The mapping locations of the reference direction on the X-ray detector are taken as the starting point for construction of the computing planes. Computing planes are formed by the focal point and the image points, that show the reference direction on the X-ray detector.

Such a projection geometry is distinguished by particular, detectable and recognizable image impressions in the first X-ray image, that may be purposefully located. For example, a torsion direction along the outermost points of the condyles may lie in a computing plane in which the condyles exactly overlap in the first X-ray image. When using a shaft direction, the reference direction may be displaced in parallel away from the shaft axis itself, so it touches, for example tangentially, the condyles that appear as one condyle. In another example, in the case of a bone that has a neck carrying a head, the first projection geometry may be selected such that the head appears in an extension of the bone shaft, whereby the torsion direction in the first computing plane points from the shaft axis laterally in the direction of the head. In this example the head would be a torsion landmark, moreover. Other cases of this kind are possible that ultimately relate to a particular, characterizing image impression in respect of the reference landmarks and the torsion landmarks.

Owing to working in the computing plane, that is defined by the focal point of the X-ray source and the position of the image points of the X-ray detector in the space at which the reference direction was recorded in the first projection geometry, is visible in the first X-ray image therefore, and owing to the reference direction expediently set at the height of the at least one torsion landmark, cone beam effects, angle deviations of other X-rays from the central beam therefore, have no relevant influence on the observations made here, so a correction in this respect is not necessary.

For the second projection geometry it is ultimately essential that the reference direction (via the at least one reference landmark) is likewise evident from the second X-ray image and that the directions of projection are different, so a second computing plane may be construed, that is given by the reference direction in the second X-ray image, accordingly in the detector plane therefore, and, again, the focal point of the now differently positioned X-ray source. The reference direction lies, by definition, in this second computing plane too. It defines the three-dimensional course of the reference direction, and therewith also the torsion direction, more accurately, and this forms the basis for determining the roll angle with respect to the comparison specification, and this will be discussed in more detail below. It is especially expedient in this case if the direction of projection of the second projection geometry is at least substantially perpendicular to the direction of projection of the first projection geometry, and this may bring advantages, for example, also in view of the then resulting image impressions and the identification capabilities of the reference landmarks and the reference direction. In the example mentioned above of the condyles that overlap in the first projection geometry, the two condyles may lie side by side in an image, likewise showing the reference direction, recorded perpendicular hereto for example in such a way that the extension of the shaft axis passes centrally between them.

Embodiments may provide, for example with regard to establishing substantially orthogonal directions of projection, that the second projection geometry is ascertained automatically from the first computing plane, for example in such a way that the central beam of the second projection geometry runs at least substantially along the surface normals of the computing plane. Automatically ascertaining the second projection geometry, for example with knowledge of the first projection geometry, may also expedient otherwise since a user may be disburdened hereby. Taking into account the first computing plane itself, for example the surface normals thereof, the second projection geometry may be adjusted as ideally as possible, however, in such a way that the computing planes are at right angles to each other as far as possible. For example, when using a fan beam geometry, as is frequently the case in X-ray facilities, an optimum right-angled relationship of the first and the second computing planes may be achieved only in rare cases, however. As will be presented below, this may be taken into account accordingly when evaluating the first and the second X-ray images.

An embodiment for ascertaining the roll angle, that works with simple vector operations, may provide for where ascertaining a measuring orthogonal system, the surface normal of the first computing plane, from the computing planes, for example by forming the cross product of the surface normals of the first and second computing planes, a three-dimensional reference vector of the reference direction describing the three-dimensional course of the reference direction and a three-dimensional torsion vector describing the three-dimensional course of the torsion direction in the first computing plane, for example by forming the cross product of the surface normals of the first computing plane and the reference vector, are determined, wherein the roll angle, as the corresponding Euler angle of the measuring orthogonal system, is ascertained as a comparison specification for a basic orthogonal system describing a basic setting of the recording arrangement.

This embodiment takes into account, for example, the fact that the first computing plane and the second computing plane as well as the surface normal of the first computing plane and the surface normal of the second computing plane do not necessarily have to be orthogonal to each other since inaccuracies in setting as well as deviations owing to the cone beam geometry and when defining the reference direction may occur. However, since the reference direction lies in both the first and in the second surface planes (per construction), it holds that both surface normals are perpendicular to it, so their cross product inevitably produces a reference vector along the reference direction irrespective of whether the surface normals are perpendicular among themselves. In any case, a torsion vector in the torsion direction is then also immediately known, namely owing to the cross product of the surface normals of the first computing plane, in which the torsion direction lies per construction, and the reference vector of the reference direction.

While, in principle, other possibilities also exist with regard to a comparison specification for assessing to what extent, compared hereto, the torsion direction is rotated about the reference direction, it nevertheless proves to be especially advantageous to work with the recognition that the surface normals of first computing plane, the reference vector and the torsion vector is an orthogonal system, called a measuring orthogonal system here. This is because the corresponding vectors are indeed known in the coordinate system of the X-ray facility, specifically of the recording arrangement. A large number of possible comparison specifications exist in this X-ray coordinate system, however, with basic positions, for example, being appropriate. If, for example, an X-ray facility with a C-arm is used, the orientation of the recording arrangement is determined, for example, from an angular angle and an orbital angle, so vectors may be used as a basic orthogonal system providing a reference, which vectors describe main directions in a basic position with angular angle zero and orbital angle zero. Of course, other basic orthogonal systems are also conceivable, however, as long as they are clearly and unambiguously defined in the X-ray coordinate system. The basic orthogonal system may, for example, also be the orthonormal system forming the basis of the X-ray coordinate system.

Among such orthogonal systems a wide variety of easy-to-implement computing techniques are now known in order to ascertain the Euler angles of one orthogonal system in relation to the other orthogonal system. The use of Euler angles is especially appropriate here since the rotation of the torsion vector about the reference vector compared to the comparison specification is being sought.

The measuring orthogonal system may be understood such that it describes the orientation of the end region of the bone, for example in the X-ray coordinate system. As already mentioned, this refers for example to the reference direction (described by the at least one reference landmark) and the torsion direction (described by the at least one torsion landmark), the directions relevant to the torsion therefore.

Whenever actually only a roll angle itself is to be determined as an item of torsion information, the comparison specification, in this specific case the basic orthogonal system, may be skillfully selected such that a desired reference, for example to the horizontal plane, is established, wherein the specific position of the bone should then also be taken into account in the interpretation and/or in the selection of the basic orthogonal system, however.

Reference should also be made to the fact that in cases in which an adequate orthogonality of the first computing plane to the second computing plane may be assumed, the surface normal of the second computing plane may be understood, optionally also directly, as a torsion vector of the torsion direction since it should then indeed lie perpendicular to the reference direction in the first computing plane. For said reasons this case cannot be reliably established in most applications, however.

The method is suitable, however, when relative torsions are to be determined, for example between the proximal and the distal end regions, it then being possible to ascertain, proximally as well as distally, a roll angle by respectively carrying out steps a) to c), and a corresponding difference may be formed. In other words, it is therefore possible to provide that for ascertaining a relative torsion angle, for example the antetorsion angle of the femur, as an item of torsion information steps a) to c) for ascertaining a digital roll angle for the distal end region and steps a) to c) for ascertaining a proximal roll angle for the proximal end region are carried out, by which the relevant torsion angle is ascertained as an item of torsion information by forming the difference between the two roll angles.

The basic concept proposed here may therefore be applied both proximally and distally in order to obtain, for example, frequently desired items of torsion information relating to the antetorsion of the bone, for example of the femur. This allows, for example, certain routines, functions, and sequences to be used repeatedly within an overall workflow therefore, and thus enable an efficient implementation. The advantage when determining a relative item of torsion information is, moreover, that the selection of the comparison specification has no influence on the obtained item of torsion information as long as it is ensured that it is kept the same. This is of interest, for example, when recording arrangements held by a mobile carrier are used, that should then remain constant in their orientation, ideally when changing from the proximal position into the distal position, or vice versa. This may customarily be assured with adequate accuracy, for example with a level floor.

Since embodiments are concerned solely with orientations, linear displacements, also between recording of the first and of the second X-ray images, ultimately have no influence on the result of measuring and ascertaining.

The procedure may be used in relation to the femur, for example with regard to determining its antetorsion angle. Specifically, it may be provided that for the femur as the bone, in the first projection geometry for the proximal end region, the extension of the femoral shaft axis, as the reference direction, runs centrally through the femoral head and/or for the distal end region, covers the femoral condyles, with the femoral shaft axis respectively, in the case of the distal end region in the first X-ray image transversely displaced in relation to a tangential course along the femoral condyle, being used as the reference direction. For the proximal end region, the direction from the femoral shaft, as the reference landmark, to the femoral head, as the torsion landmark, may be used as the torsion direction therefore. The torsion direction thus runs in the projection on a plane perpendicular to the femoral shaft axis in the same way as the femoral neck axis, that is used by definition for ascertaining the antetorsion angle. This means, with regard to determining a roll angle about the reference direction, given here by the femoral shaft axis, the torsion direction thus determined is equivalent to the femoral neck axis.

For the distal end region, the direction in the condyle plane running from femoral condyle to femoral condyle as the torsion landmarks, is used as the torsion direction. The torsion direction therefore lies in the condyle plane, for example perpendicular to the shaft axis. For the correct selection of the first computing plane as the one containing the condylus apexes, the reference direction is displaced parallel with respect to the femoral shaft axis, so it runs tangentially along the femoral condyle. It is pointed out in this connection that a displacement in the second X-ray image with approx. 900 difference between the directions of projection is not necessary since the femoral shaft axis should then run centrally between the femoral condyles.

In an embodiment for determining the antetorsion angle of the femur, the torsion of the proximal femur is determined. This exploits the fact that the femoral shaft and the femoral head are easy to identify as landmarks in the X-ray images. A first projection geometry is ascertained or set here in such a way that the extension of the femoral shaft axis runs through the center of the femoral head in the first X-ray image. The course of the femoral shaft axis specifies the reference direction, that together with the focus of the X-ray source spans a first computing plane, that contains both the femoral head and the femoral shaft axis. The orientation of this first plane and its surface normal in the space may be automatically calculated on the basis of the set first projection geometry and the known beam geometry of the recording arrangement.

In a further step of this embodiment relating to the femur, the second projection geometry may now be automatically determined by the X-ray facility in such a way that the central beam lies parallel to the surface normal of the first computing plane. After adopting this second projection geometry a second X-ray image of the proximal femur is recorded, so now the second computing plane in the space may be defined on the basis of the femoral shaft axis as the reference direction, for which purpose a surface normal may likewise be calculated. As explained above, with the aid of the two surface normals, the reference vector and the torsion vector, for example, may then be ascertained, that together with the surface normal of the first computing plane define a measuring orthogonal system, that may be understood as the basis of a measuring coordinate system. The measuring orthogonal system describes the position of the proximal femur in the space. If the Euler transformation is now calculated relative to the comparison specification, for example the basic orthogonal system, that may be conceived of as the reference coordinate system, the corresponding Euler angle is obtained. The roll angle defines the rotation of the femur about the shaft axis, precisely the torsion of the proximal femur therefore, with appropriate selection of the comparison specification relative to the horizontal.

The torsion of the distal femur, described by a further roll angle relative to the same comparison specification, may then be determined in this embodiment. This follows the above-described procedure very closely since, ultimately, steps a) to c) are again carried out. In contrast to the femoral head, the condyle plane is used here as an anatomical marker, a torsion landmark therefore, in addition to the femoral shaft as a reference landmark. In this determination of the roll angle the first projection geometry is selected such that the femoral condyles are at the same height or overlap exactly. A straight line, that runs parallel to the femoral shaft axis and tangential to the condyles is now used here as a reference direction. Accordingly, the first computing plane and the surface normal of the first computing plane may be ascertained. The procedure is analogous to the case of the proximal end region of the femur in the following steps b) and c), with the accordingly calculated roll angle in this case corresponding to the torsion of the condyle plane. The femoral antetorsion angle then corresponds to the difference between the torsion of the proximal femur and that of the distal femur, the difference between the two roll angles therefore.

One general advantage of this procedure is that the determination of the item of torsion information, for example of the antetorsion angle, is enabled with a high level of accuracy on the basis of individual X-ray images despite a fast and straightforward practicability. The exposure of the patient to radiation is significantly reduced since only a few X-ray images are required. The method is basically also suitable for intraoperative use, so postoperative computed tomography scans and revision operations may be avoided.

Some of the steps may be carried out by a user, for example a doctor or another medical member of staff. The first projection geometry may be discovered by varying the position and/or the orientation of the recording arrangement such that the desired image impression results. With regard to the determination of the reference direction in the first or in the second X-ray image too, a user may be called on, for example prompted to do this. Embodiments provide more extensive automation, however, by using suitable, for example trained, evaluation functions.

Embodiments provide that the first projection geometry is automatically ascertained at least before carrying out step a) by evaluating at least one orientation image of the X-ray facility in at least one orientation geometry and/or ascertaining the reference direction in the first and/or second X-ray image(s) in steps a) and b) by at least one, for example trained, evaluation function. In this way, the temporal efficiency and user friendliness of the method is advantageously increased further.

In this connection it is possible to provide, for example, that artificial intelligence is used, artificial intelligence evaluation functions trained at least partially by machine learning, therefore.

In general, a trained function maps cognitive functions that humans associate with other human brains. By way of training based on training data (machine learning) the trained function is capable of adapting to new circumstances and of detecting and extrapolating patterns.

Generally speaking, parameters of a trained function may be adapted by training. For example, supervised learning, semi-supervised learning, unsupervised learning, reinforcement learning and/or active learning may be used. Furthermore, representation learning (also known as "feature learning") may also be used. The parameters of the trained function may be adapted, for example iteratively, by a plurality of training steps.

A trained function may include, for example, a neural net, a Support Vector Machine (SVM), a decision tree and/or a Bayesian network and/or the trained function may be based on k-means clustering, Q-learning, genetic algorithms and/or assignment rules. For example, a neural network may be a deep neural network, a Convolutional Neural Network (CNN) or a deep CNN sein. Furthermore, the neural network may be an Adversarial Network, a deep Adversarial Network and/or a Generative Adversarial Network (GAN).

Trained evaluation functions may be used for image evaluation, for example with regard to the detection or localization of landmarks and/or for identifying and interpreting other image features. It is advantageous in this connection if at least one of the at least one trained evaluation functions include a Convolutional Neural Network (CNN).

In a specific embodiment it may be provided that for ascertaining the first projection geometry, at least one orientation landmark of the bone is detected by at least one trained one of the evaluation functions. For example, at least two orientation landmarks, for example including at least one of the at least one torsion landmarks, may be detected by respective trained evaluation functions whose output data is combined for ascertaining a three-dimensional item of orientation information of the bone and, from this, the first projection geometry. In this case it should first of all basically be noted that reference landmarks and torsion landmarks may serve as orientation landmarks. At least one torsion landmark is used as the orientation landmark, however, since after its detection, for example segmenting, it is possible to calculate how the image impression, that should result in the first projection geometry, and thus also the possibility of defining the corresponding first computing plane, may result. For example, a consideration of the femoral condyle and of the femoral shaft may be used as orientation landmarks for the distal femur, while the femoral head and/or the femoral neck and/or the femoral shaft may be used as orientation landmarks for the proximal femur, as the proximal end region of the femur. In this way, a user may be provided with at least one aid for discovering the first projection geometry.

In an embodiment it may also be provided that at least one of the at least one trained evaluation functions was trained for ascertaining the first projection geometry at least partially by computed tomography projection image sets. Projection image sets of this kind usually sample the end region of a bone in close angular increments, so the projection image of the projection image set suitable for a first projection geometry may be annotated. It is then possible to learn how the marked projection image may be inferred from the other projection images. The thus trained evaluation algorithm may then conclude from an orientation image, as the input data, the first projection geometry, as the output data, for example internally on the basis of orientation landmarks.

For ascertaining the reference direction, at least one of the at least one reference landmarks may be detected by at least one trained one of the evaluation functions. Methods have already been proposed in the prior art, for example in respect of detection of the shaft axis, in order to detect this axis with the aid of artificial intelligence, that may also be used.

In such a case, but also generally, for example in view of ascertaining the first projection geometry, it may be provided that when the shaft axis (or the bone shaft) is used as an orientation landmark and/or reference landmark, a probability map of the course of the shaft axis is ascertained by a trained evaluation function, by which a straight line is fitted in the probability map for ascertaining the shaft axis. The probability map may output, for example, probabilities that the corresponding image point pertains to the shaft of the bone or even to the shaft axis. It is then possible, by customary fit programs, to evaluate such probability maps in order to ascertain therefrom a course of a shaft axis, that is then suitable as a straight line for defining the reference direction.

In an embodiment, when ascertaining an orientation landmark and/or reference landmark describing the position of the respective end region in respect of the second projection geometry, a linear adjusting facility of the recording arrangement of the X-ray facility is automatically actuated for compensating a position of the end region outside of the recording region of the recording arrangement in the second projection geometry while maintaining its direction of projection. In some cases the situation may occur where, when setting a second projection geometry, that was defined solely on the basis of a suitable, altered direction of projection with respect to the first projection geometry, the end region of the bone that is actually of interest slips out of the recording region. Since embodiments are primarily concerned with orientations, linear adjusting facilities associated with the recording arrangement may be used to achieve a suitable image detail, and this may also occur automatically accordingly with knowledge of the position of orientation landmarks and/or reference landmarks of the bone relative to the recording arrangement. The user may also use appropriate adjusting facilities when the end region of the bone should initially not lie in the image in the second projection geometry. In general, suitable adjusting facilities in this context are, for example, a lifting column and/or a horizontal displacement facility.

In general, actuatable adjusting devices, for example having suitable actuators may also include, optionally in addition to the linear adjusting facilities, adjusting devices for the corresponding orientation settings of the recording arrangement. Embodiments provide that the first and/or the second projection geometry/geometries is/are set at least partially automatically by actuation of adjusting devices associated with the recording arrangement. In this way, the projection geometries may be accurately set and users are further disburdened.

Expediently, a flat-panel detector may be used as the X-ray detector. Flat-panel detectors have the advantage that geometric distortions do not have to be taken into account when the first and the second planes are construed since the position of the receiving pixels along the reference straight lines directly reproduce the corresponding position in the space.

Specifically, the X-ray facility may be an X-ray facility with a mobile C-arm to which the recording arrangement is attached. The position of the mobile C-arm may preferably remain constant during steps a) to c) respectively, for example when its position cannot be adequately accurately tracked. Reference should be made once again in this connection to the fact that a change in the position of the mobile C-arm is definitely possible, however, if a changeover is made from a measurement in the proximal end region to the distal end region, or vice versa. This is because here it is only a matter of the corresponding orientations, that may be assumed to be identical in both positions, at least with a level floor.

In addition to the method, embodiments also relate to an X-ray facility, for example an X-ray facility with a mobile C-arm. The X-ray facility has a recording arrangement, that includes an X-ray source and an X-ray detector, whose projection geometry may be set described by projection parameters. With a C-arm, the X-ray source, and the X-ray detector, for example, may face each other on the C-arm. The X-ray facility is characterized in that it has a control facility configured for carrying out the method. All statements in respect of the method may be analogously transferred to the X-ray facility with which the advantages already described may likewise be obtained.

The control facility may include at least one processor and at least one storage, it being possible for, for example, functional units for carrying out steps of the method to be provided by the processor. Here, the control facility may have, for example, a recording unit controlling the recording operation of the X-ray facility, for example also for recording the first X-ray image and the second X-ray image. The recording unit may be used by roll angle-ascertaining units to bring about recording of the first and second X-ray images, that are respectively required. The roll angle-ascertaining unit may include, for example, a plane-ascertaining subunit and a roll angle-calculating subunit for constructing the planes, ascertaining surface normals and for ultimate calculation of the roll angle. Furthermore, the control facility may have an item of torsion information-ascertaining unit to ascertain or compile the item of torsion information from the roll angle. Further functional units according to embodiments are of course also conceivable.

A computer program may be directly loaded into the memory of a control facility of an X-ray facility and has program code, that carry out the steps of a method when the computer program is executed in the control facility of the X-ray facility. The computer program may be stored on an electronically readable data carrier, that includes items of control information stored thereon, that include at least one computer program and are configured in such a way that when the data carrier is used in a control facility of an X-ray facility, the facility is configured to carry out the steps of the method when the computer program is executed.

DETAILED DESCRIPTION

Figure 1:
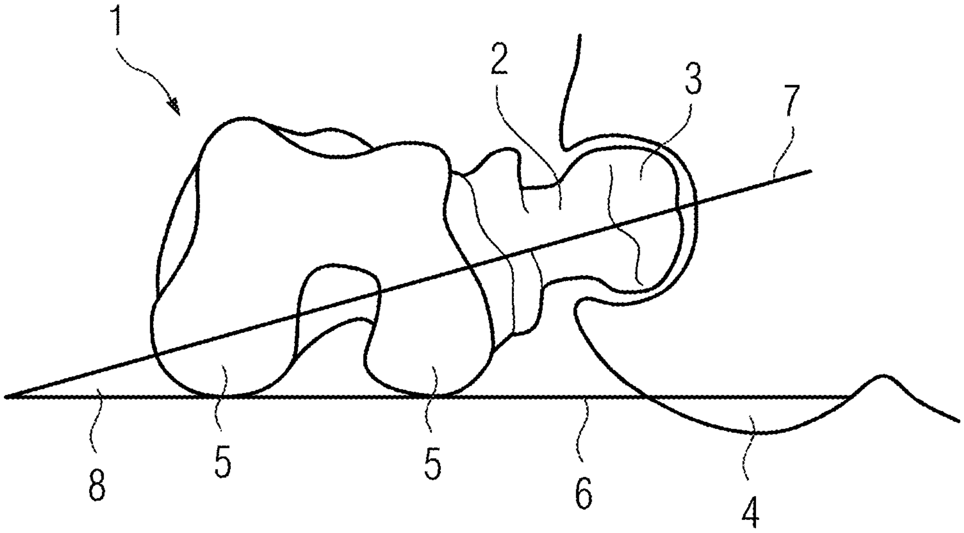
FIG. 1 depicts a distal view of a femur in the direction of its shaft axis.

An embodiment of the method in an application to the femur as the bone is described below. The method may also be analogously applied to other bones, wherein the humerus should be cited purely by way of example.

The antetorsion angle of the femur is determined in the embodiment now discussed in more detail. This shall be illustrated in more detail by FIG. 1, that depicts a view of the femur 1 starting from distal, along the shaft axis as the viewing direction. The femoral neck 2 and the femoral head 3 may accordingly also be seen proximally; the pelvic girdle 4 is indicated. The femoral condyles 5 may be clearly identified at the knee-side, distally therefore. It is evident that there is a rotation between the condyle plane 6 and the femoral neck shaft 7, which rotation is referred to as antetorsion and may be described by an antetorsion angle 8, that describes the torsion in the proximal and distal end regions relative to each other.

The antetorsion angle 8, as an item of torsion information, shall now be determined on the basis of X-ray images in a particularly time-efficient manner, with low radiation and simply in such a way that the method described below may be used, for example, also intraoperatively to be able to check, for example before locking a femoral nail, whether the antetorsion has been correctly re-established. The method may also be used in other ways, however, for example in a diagnostic context. In the present case, an X-ray facility with a C-arm is used as the X-ray facility, on which arm an X-ray source and an X-ray detector, that form a recording arrangement, are arranged facing each other. A flat-panel detector is used as the X-ray detector. To be able to set different projection geometries, for example also different directions of projection, the X-ray facility optionally has actuatable adjusting devices, that, in addition to setting options for an angular angle (rotation of the C-arm about its central axis) and an orbital angle (displacement along its circumference) may also include adjusting facilities for linear adjustments, for example a lifting column for the height setting and/or a linear guide for a lateral, horizontal adjustment. The C-arm is mobile and may thus be positioned in different ways in the space whose floor is assumed to be at least substantially level.

Figure 2:
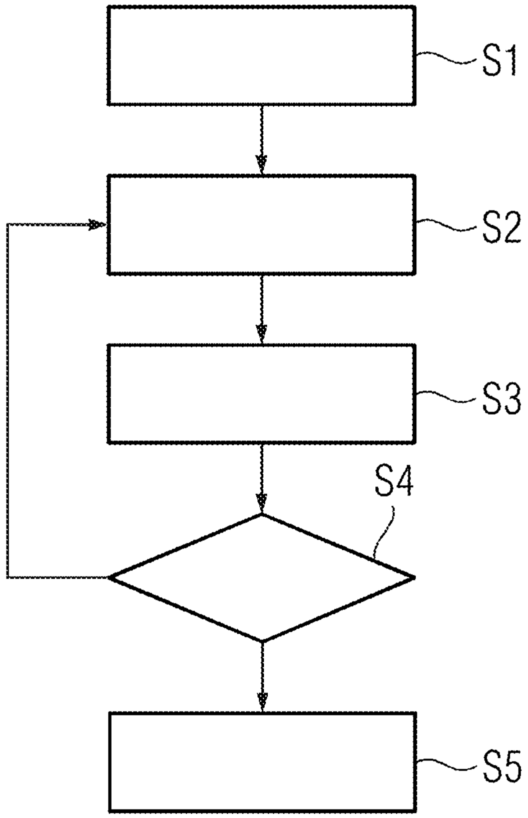
FIG. 2 depicts a flowchart of an embodiment of a method.

According to FIG. 2, the method for determining the antetorsion angle 8 as an item of torsion information begins in a step S1. A patient is already positioned on a patient couch of the X-ray facility here, for example on an operating table.

A choice is then made as to whether to begin with the distal end region (knee region) or the proximal end region (hip region). The corresponding end region of the femur is approached in a step S2 by the mobile C-arm, and this is possible by way of a user and/or at least partially automatically.

A sequence of substeps then takes place in a step S3, by which, as will be explained in more detail, a roll angle is determined with respect to a comparison specification, identical for both end regions, for the respective end region.

It is then checked in step S4 whether roll angles have already been determined for both end regions of the bone, here of the femur, wherein, if not, steps S2 and S3 are repeated for the other end region; if so, the antetorsion angle 8 is ascertained in a step S5 by forming the difference between the two roll angles and forms an item of torsion information, that may be output, for example on a display, and/or be stored in a storage.

Figure 3:
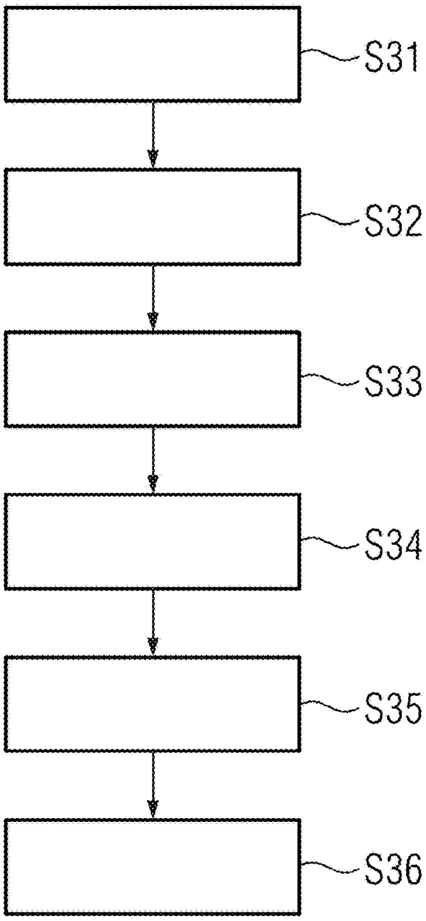
FIG. 3 depicts steps of a repeated method step of FIG. 2 according to an embodiment.

FIG. 3 depicts a general flowchart of substeps of step S3 in order to ascertain the roll angle. At least the measures a) to c) discussed in the general description are implemented.

Thus, in a substep S31 a first projection geometry is set in which a first X-ray image of the respective end region of the femur 1 is then recorded. The first projection geometry is selected such that a torsion direction defined relative to at least one torsion landmark to be used for ascertaining the roll angle lies in a first computing plane, that is formed by the focal point of the X-ray source and a reference direction that may be determined in the first X-ray image by at least one reference landmark, for example parallel to the shaft axis of the femur 1. Here, the reference direction is considered in the space where it was measured, at the respective image points of the X-ray detector in the detector plane therefore. The first projection geometry is associated with an image impression of the at least one torsion landmark in a corresponding X-ray image.

In order to discover this first projection geometry a user may change the orientation of the recording arrangement until the desired image impression results. An orientation image may be recorded from which, by at least one trained evaluation function, for example a CNN, the first projection geometry may be ascertained, for which purpose orientation landmarks, for example, for example themselves including the torsion landmark and/or the reference landmark, may be analyzed. For example, the trained evaluation algorithm uses the orientation image as input data and may output the first projection geometry absolutely or as adjusting instructions, relatively therefore, as output data, with the adjusting instructions also being suitable for corresponding actuation when suitable actuatable adjusting devices are available. For example, projection images of a computed tomography recording of a corresponding bone may also be used for training this first evaluation function, in which images the projection image whose image impression is sought as the first projection geometry is annotated accordingly.

Training approaches that use computed tomography projection images for training, in which, advantageously, image impressions from a large number of directions of projection, using a large number of projection geometries therefore, are present, that may be associated with orientation images, may be used not only in the case of the femur, but may also be applied in the case of other bones accordingly.

The corresponding construction of this first computing plane and ascertaining its surface normal then take place in a substep S32. While a user may use the at least one reference landmark, that may be identified in the first X-ray image, in order to mark the reference direction, an embodiment may also provide the use of evaluation algorithms, for example trained evaluation algorithms. For example, using neural nets, for example CNNs that supply a probability map for the femoral shaft axis as output data, it the corresponding reference direction may be ascertained, or shaft axis, from the probability map by fitting a straight line.

A suitable second projection geometry for a second X-ray image is ascertained in a substep S33 and manually and/or at least partially automatically set accordingly, with the position of the stand of the mobile C-arm remaining constant, however. The second projection geometry is ascertained, by way of example, such that the central beam of the second projection geometry runs at least substantially along the surface normals of the first computing plane. Other directions of projection of the second projection geometry may also be used, however, as long as they differ sufficiently from the direction of projection of the first projection geometry. If the end region of the femur should not lie in the recording region of the recording arrangement after setting the second projection geometry, linear adjusting facilities of the C-arm may be used to compensate, for example a height-adjusting facility and/or a lateral adjusting facility in the horizontal. This may also take place automatically, for example if anatomical landmarks were determined automatically.

The second X-ray image is recorded in a substep S34. The second computing plane may accordingly be construed in a substep S35, it being possible to again determine the reference direction at least partially manually and/or at least partially automatically, preferably fully automatically, for example using the trained evaluation algorithm, that supplies a probability map of the femoral shaft axis. The surface normal relative to the second computing plane is also determined.

With this know-how it is now possible to automatically determine the roll angle in step S36. The cross product of the surface normals of the first and the second computing planes is formed in order to obtain a reference vector, that describes the three-dimensional course of the reference direction. If the cross product of the surface normals of the first computing plane is now formed with the reference vector, the torsion vector showing the three-dimensional course of the torsion direction is obtained. The roll angle, as the rotation of the torsion direction and the reference direction with respect to a comparison specification, may accordingly be ascertained from this. Specifically, it is possible to exploit the fact that the reference vector, the torsion vector, and the surface normal of the first computing plane form an orthogonal system, that may be referred to as the measuring orthogonal system. The measuring orthogonal system may be understood as the basis of a measuring coordinate system describing the orientation of the femur. These items of information are all present in the X-ray coordinate system of the recording arrangement in which a basic orthogonal system defined for example with regard to a basic position (for example angular angle and orbital angle 0) may also exist, for example as a basis. The roll angle may then be ascertained by ascertaining the Euler transformation between these two orthogonal systems or coordinate systems.

The specific procedures for the proximal end region of the femur 1 and the distal end region of the femur 1 will now be explained in more detail below. This shall begin with the proximal end region, the hip-side end region therefore.

Figure 4:
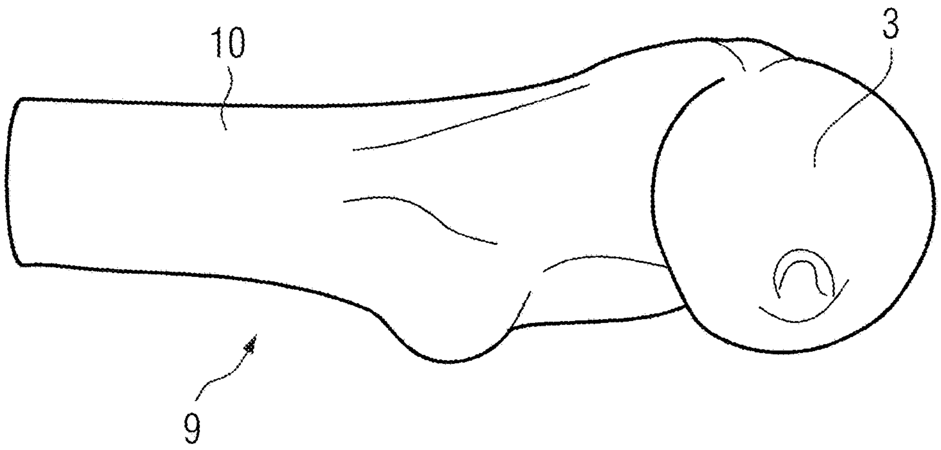
FIG. 4 depicts a view of a proximal end region of the femur in a first projection geometry according to an embodiment.

For this, FIG. 4 depicts a schematic, perspective view of the proximal end region 9 of the femur 1 in a view or an image impression as is desired for the first projection geometry. It may be seen that the extension of the femoral shaft 10 goes centrally through the femoral head 3, and this thus also applies to the shaft axis of the femoral shaft 10. This means, however, that the portion of the neck axis of the femoral neck 2 relevant to the torsion runs perpendicular, toward the viewer therefore, so the first computing plane will contain this relevant portion—the torsion direction—as is evident by construction.

Figure 5:
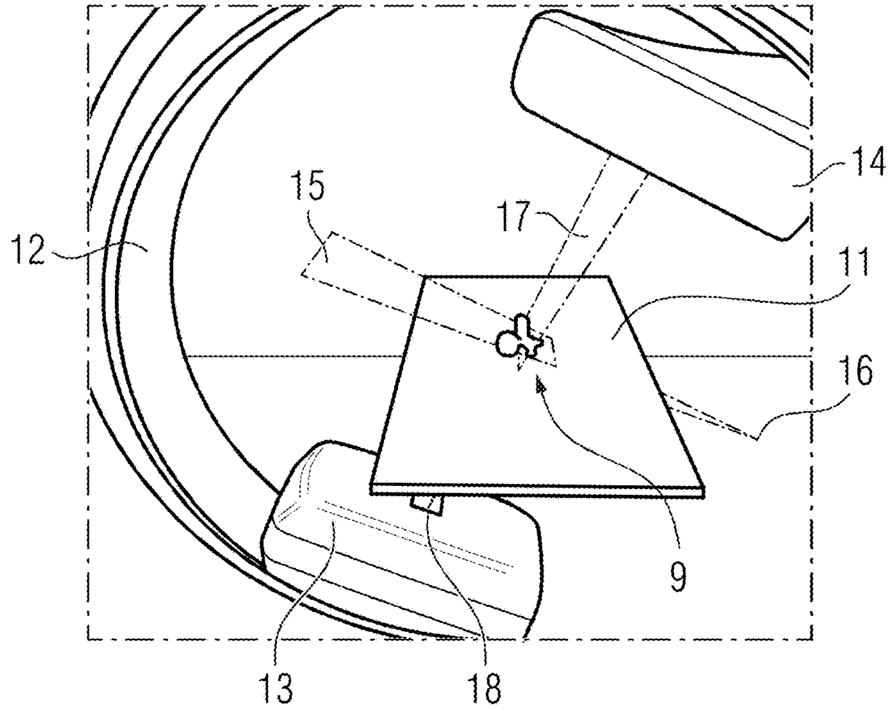
FIG. 5 depicts a perspective view of a femur with indicated reference planes according to an embodiment.

FIG. 5 schematically depicts the proximal end region 9 on a patient couch 11 in the context of the C-arm 12 with the X-ray source 13 and the X-ray detector 14, that are shown already in the setting for the second projection geometry, however. The partially indicated first computing plane 15 is defined by the focal point 16 of the X-ray source 13 in the first projection geometry and the shaft axis of the femoral shaft 10 as the reference direction. The direction of projection of the second projection geometry is at least substantially perpendicular to the direction of projection of the first projection geometry and permits the definition of the second computing plane 17 again by the shaft axis of the femoral shaft 10 as the reference direction and the focal point 18 of the X-ray source 13 in the second projection geometry.

Figure 6:
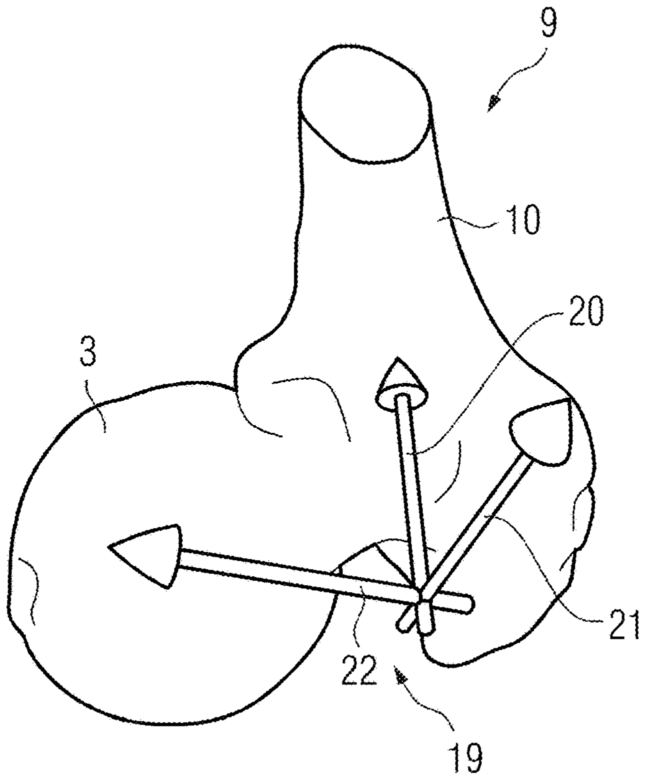
FIG. 6 depicts a perspective view of the proximal end region of the femur with a measuring orthogonal system according to an embodiment.

FIG. 6 schematically depicts the resulting measuring orthogonal system 19 in the context of the proximal end region 9. The reference vector 20 points along the reference direction, the femoral shaft axis, that was determined on the basis of the corresponding reference landmark, of the femoral shaft 10. The first computing plane permits the construction of its surface normals 21, with the torsion vector 22 indicating the torsion direction being shown perpendicular to both, which vector evidently points through the femoral head 3 (torsion landmark). The roll angle, that is being sought, is the rotation of the torsion vector 22 about the reference vector 20 with respect to a comparison specification, that in the present case, as long as it is selected to be identical for both end regions, is arbitrary since it is, indeed, a matter of a relative item of torsion information, specifically the antetorsion angle 8.

Figure 7:
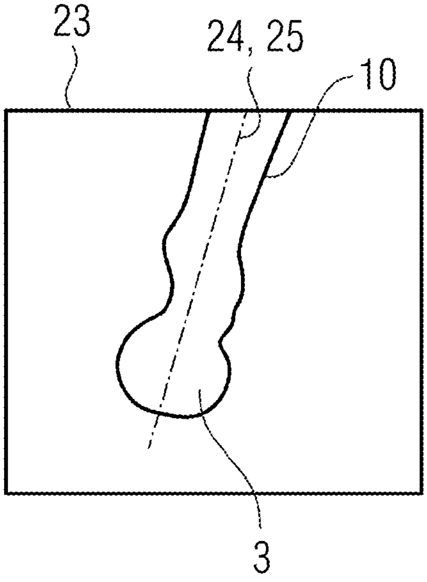
FIG. 7 schematically depicts a first X-ray image of the proximal end region of the femur according to an embodiment.

FIG. 7 schematically depicts a first X-ray image 23 in which, as may clearly be seen, the extension of the femoral shaft axis 24, as the reference direction 25, runs centrally through the femoral head 3. If the femoral shaft axis 24 is known in the first X-ray image 23, it is also known with which image points of the X-ray detector 14 it was recorded, so the first plane 15 may be easily construed by the focal point 16 and these image points in the detector plane.

Figure 8:
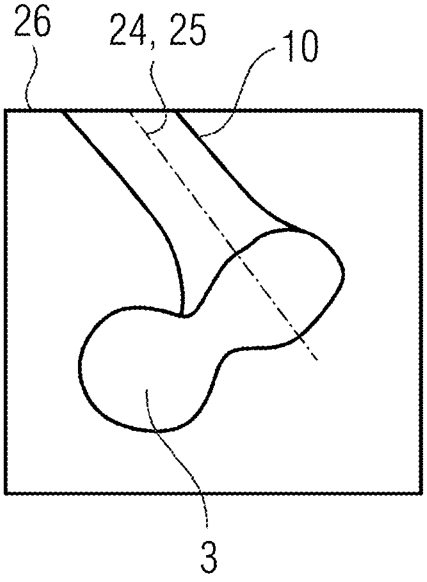
FIG. 8 schematically depicts a second X-ray image of the proximal end region of the femur according to an embodiment.

Accordingly, FIG. 8 schematically depicts a second X-ray image 26 in which the femoral shaft axis 24 is again shown as the reference direction 25, with the femoral head 3 now accordingly being turned outwards as expected.

Figure 9:
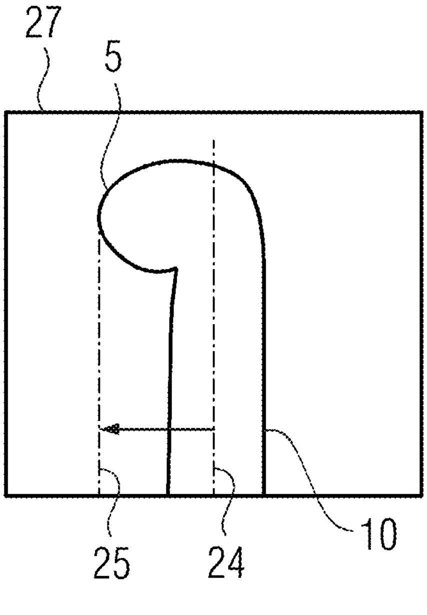
FIG. 9 schematically depicts a first X-ray image of the distal end region of the femur according to an embodiment.

A comparable procedure may be used in the distal end region of the femur 1. The first projection geometry is selected such that it covers femoral condyles 5 in the first X-ray image. This means they seem like one femoral condyle 5. FIG. 9 schematically depicts a corresponding first X-ray image 27. Due to the overlapping, the femoral condyles 5 evidently act like just a single condyle, although the femoral shaft 10 may of course also clearly be seen. In order for the first reference plane 15 to lie correctly, namely also in the region of the condyle plane 6, the femoral shaft axis 24 is not used directly as the reference direction 25 here, however, and instead the shaft axis 24 is displaced in parallel until it tangentially abuts the condyles 5 in order to define the reference direction 25.

Figure 10:
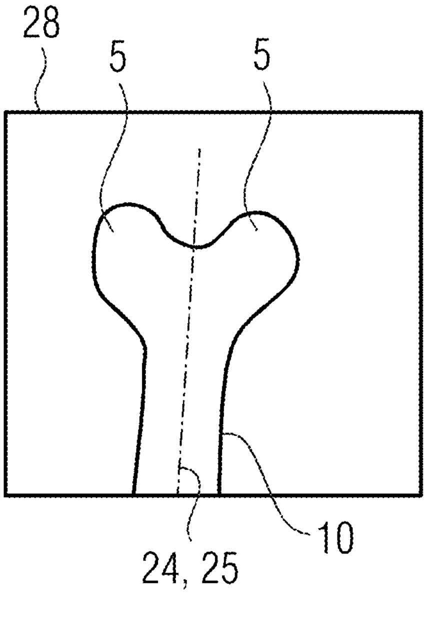
FIG. 10 schematically depicts a second X-ray image of the distal end region of the femur according to an embodiment.

In the second projection geometry, at least when its direction of projection is at least substantially perpendicular to the direction of projection of the first projection geometry, in the second X-ray image 28, cf. the schematic representation in FIG. 10, the femoral shaft axis 24 lies in any case at least substantially centrally between the femoral condyles 5, so it may form the reference direction 25.

It should also be noted at this point that the measuring orthogonal system may ultimately also be understood as showing the orientation of the respective end regions 9 and that the comparison orthogonal system may also be purposefully selected such that a desired reference may be established also for individual end regions 9. For example, torsions against the horizontal may thus be determined.

If the roll angles in the case of the femur are ascertained by running through step S3 twice, as explained with reference to FIG. 4 to 10, the sought antetorsion angle 8 then results from their difference. If, for example, roll angles of −26° proximally and −3° distally are ascertained, the resulting antetorsion is −26°−(−3°)=−23°.

Figure 11:
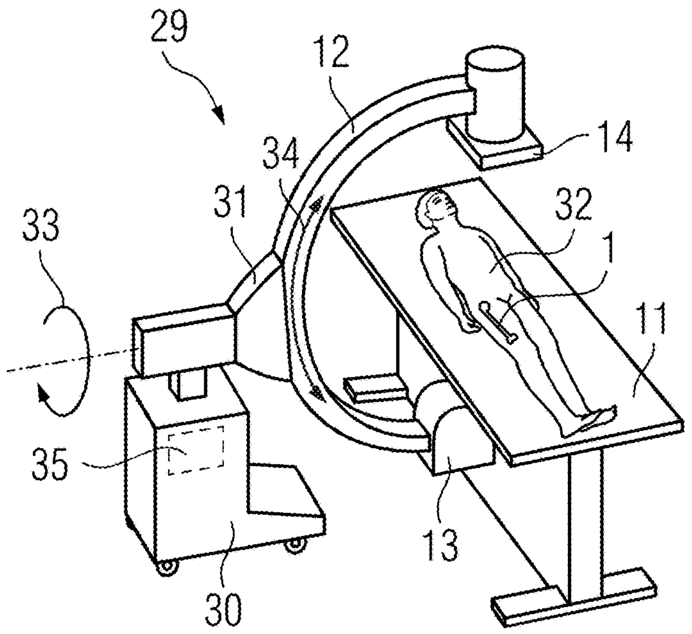
FIG. 11 depicts a schematic diagram of an X-ray facility according to an embodiment.

FIG. 11 depicts a schematic diagram of an X-ray facility 29. The X-ray facility includes, as already explained in respect of FIG. 5, the C-arm 12 on which the X-ray source 13 and the X-ray detector 14 are arranged facing each other. The C-arm 12 is configured as a mobile C-arm 12 and arranged on a correspondingly movable stand 30. Different projection geometries of the recording arrangement formed from the X-ray source 13 and the X-ray detector 14, that is a flat-panel detector, may be set relative to a patient 32 here by merely indicated adjusting device 31. For example, a rotation of the C-arm 12 about an angular angle, cf. arrow 33, and a displacement of the C-arm 12 for tilting about an orbital angle according to arrow 34 is possible. The adjusting device 31 may include adjusting facilities for linear adjustment, for example a lifting column and/or a horizontal guide.

Figure 12:
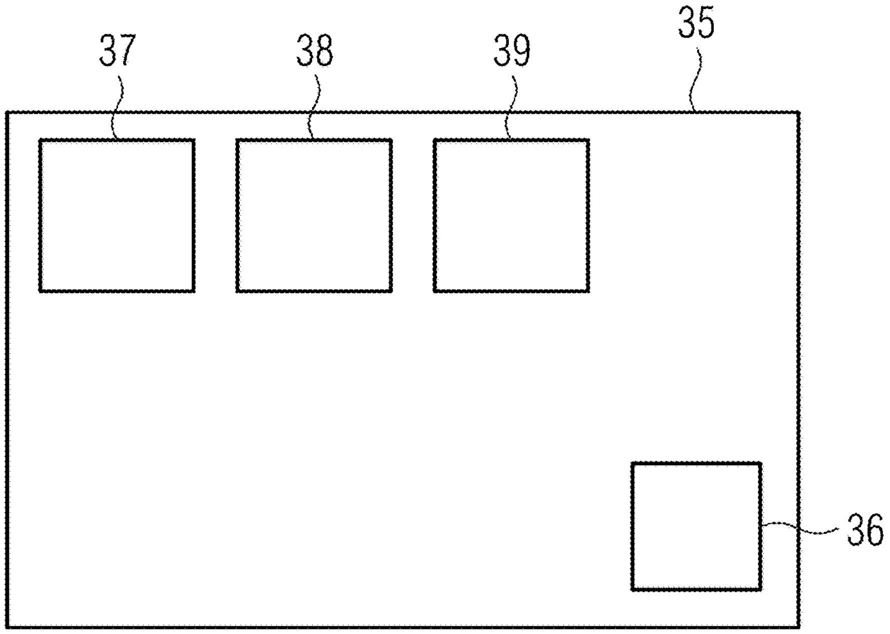
FIG. 12 depicts the functional structure of the control facility of the X-ray facility according to an embodiment.

Operation of the X-ray facility 29 is controlled by a control facility 35, only indicated in FIG. 1, that is configured for carrying out the method and whose functional structure is explained in more detail with regard to FIG. 12. Accordingly, the control facility 35 includes a storage 36 in which the X-ray images 23, 26, 27 and 28, intermediate results and/or end results such as the item of torsion information may be stored. A recording unit 37 controls the recording operation of the X-ray facility 29. Recording of the first and second X-ray images 23, 26, 27, 28 according to substeps S32 and S34, for example, may also be controlled by the recording unit 37. Recording of an orientation image, if provided, in substep S31 may also be controlled by the recording unit 37.

The control facility 35 includes a roll angle-ascertaining unit 38 for carrying out the calculations and ascertainments of steps S2 to S4, which unit may have various ascertaining subunits (not shown here), for example at least one plane-ascertaining subunit and one roll angle-calculating subunit for carrying out steps S32/S35 and S36 respectively. Further subunits may include evaluation subunits for the application of, for example trained, evaluation functions and projection geometry-ascertaining subunits (for example step S31, step S33).

The item of torsion information may then be ascertained according to step S5 from the roll angles or the at least one roll angle in an item of torsion information-ascertaining unit 39.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for ascertaining an item of torsion information of a bone, of a patient, wherein an X-ray facility with adjustable projection geometry of a recording arrangement described by projection parameters is used, the X-ray facility comprising an X-ray source and an X-ray detector, the method comprising:

recording a first X-ray image of an end region of the bone in a first projection geometry in which a torsion direction defined relative to at least one torsion landmark and used for ascertaining a roll angle lies in a first computing plane, which is formed by a focal point of the X-ray source and a reference direction that is determined in the first X-ray image by at least one reference landmark;

recording a second X-ray image of the end region of the bone in a second projection geometry with a direction of projection deviating from the direction of projection of the first projection geometry and forming a second computing plane from the reference direction that is determined in the second X-ray image by the at least one reference landmark, and the focal point; and ascertaining a three-dimensional course of the reference direction and the torsion direction from the first computing plane, the second computing plane, and the roll angle as a rotation of the torsion direction about the reference direction with respect to a comparison specification;

wherein the item of torsion information is ascertained from the roll angle.

2. The method of claim 1, wherein the second projection geometry is ascertained from the first computing plane in such a way that a central beam of the second projection geometry runs at least substantially along a surface normal of the first computing plane.

3. The method of claim 1, wherein ascertaining a measuring orthogonal system comprises determining a surface normal of the first computing plane, a three-dimensional reference vector of the reference direction describing the three-dimensional course of the reference direction from the first computing plane and the second computing plane by forming a cross product of surface normals of the first computing plane and the second computing plane, and a three-dimensional torsion vector describing the three-dimensional course of the torsion direction in the first computing plane by forming the cross product of the surface normals of the first computing plane and the three-dimensional reference vector;

wherein the roll angle, as the corresponding Euler angle of the measuring orthogonal system, is ascertained as a comparison specification for a basic orthogonal system describing a basic setting of the recording arrangement.

4. The method of claim 1, wherein the bone comprises a femur; and wherein in the first projection geometry for a proximal end region, an extension of a femoral shaft axis that is used as the reference direction runs centrally through a femoral head and/or for a distal end region and covers a femoral condyles, wherein the distal end region in the first X-ray image transversely displaced in relation to a tangential course along the femoral condyle and the femoral shaft axis is used as the reference direction.

5. The method of claim 1, wherein for ascertaining a relative torsion angle as an item of torsion information, recording the first X-ray image, recording the second X-ray image, and ascertaining are performed for ascertaining a distal roll angle for a distal end region and for ascertaining a proximal roll angle for a proximal end region; wherein after which the relative torsion angle is ascertained as an item of torsion information by forming a difference between the distal roll angle and the proximal roll angle.

6. The method of claim 1, wherein the first projection geometry is automatically ascertained at least before carrying out recording the first X-ray image by evaluating at least one orientation image of the X-ray facility in at least one orientation geometry and/or ascertaining the reference direction in the first X-ray image, the second X-ray image, or the first X-ray image and the second X-ray image by at least one evaluation function.

7. The method of claim 6, wherein for ascertaining the first projection geometry, at least one of the at least one torsion landmarks is detected by respective trained evaluation functions whose output data is combined for ascertaining a three-dimensional item of orientation information of the bone and, from the three-dimensional item of orientation information, the first projection geometry, and/or for ascertaining the reference direction, at least one of the at least one reference landmarks is detected by at least one trained one of the evaluation functions.

8. The method of claim 7, wherein a shaft axis is used as an orientation landmark, reference landmark, or orientation landmark and reference landmark, wherein a probability map of the course of the shaft axis is ascertained by a trained evaluation function, by which a straight line is fitted in the probability map for ascertaining the shaft axis.

9. The method of claim 8, wherein in that when ascertaining an orientation landmark and/or a reference landmark describing a position of the respective end region in respect of the second projection geometry, a linear adjusting facility of the recording arrangement of the X-ray facility is automatically actuated in order to compensate a position of the end region outside of a recording region of the recording arrangement in the second projection geometry while maintaining its direction of projection.

10. The method of claim 1, wherein the first projection geometry and/or the second projection geometry is set at least partially automatically by actuating adjusting devices associated with the recording arrangement.

11. The method of claim 1, wherein a flat-panel detector is used as the X-ray detector.

12. The method of claim 1, wherein the X-ray facility includes a mobile C-arm, to which the recording arrangement is attached, wherein a position of the mobile C-arm remains constant.

13. An X-ray facility with adjustable projection geometry of a recording arrangement described by projection parameters, the X-ray facility comprising:

an X-ray source; and an X-ray detector, the X-ray detector comprising a control facility configured to:

record a first X-ray image of an end region of a bone in a first projection geometry in which a torsion direction defined relative to at least one torsion landmark and used for ascertaining a roll angle lies in a first computing plane, which is formed by a focal point of the X-ray source and a reference direction that is determined in the first X-ray image by at least one reference landmark;

record a second X-ray image of the end region of the bone in a second projection geometry with a direction of projection deviating from the direction of projection of the first projection geometry and forming a second computing plane from the reference direction that is determined in the second X-ray image by the at least one reference landmark, and the focal point; and ascertain a three-dimensional course of the reference direction and the torsion direction from the first computing plane, the second computing plane, and the roll angle as a rotation of the torsion direction about the reference direction with respect to a comparison specification;

wherein an item of torsion information is ascertained from the roll angle.

14. The X-ray facility of claim 13, wherein the second projection geometry is ascertained from the first computing plane in such a way that a central beam of the second projection geometry runs at least substantially along a surface normal of the first computing plane.

15. The X-ray facility of claim 13, wherein ascertaining a measuring orthogonal system comprises determining a surface normal of the first computing plane, a three-dimensional reference vector of the reference direction describing the three-dimensional course of the reference direction from the first computing plane and the second computing plane by forming a cross product of surface normals of the first computing plane and the second computing plane, and a three-dimensional torsion vector describing the three-dimensional course of the torsion direction in the first computing plane by forming the cross product of the surface normals of the first computing plane and the three-dimensional reference vector;

wherein the roll angle, as the corresponding Euler angle of the measuring orthogonal system, is ascertained as a comparison specification for a basic orthogonal system describing a basic setting of the recording arrangement.

16. The X-ray facility of claim 13, wherein the bone comprises a femur; and wherein in the first projection geometry for a proximal end region, an extension of a femoral shaft axis that is used as the reference direction runs centrally through a femoral head and/or for a distal end region and covers a femoral condyles, wherein the distal end region in the first X-ray image transversely displaced in relation to a tangential course along the femoral condyle and the femoral shaft axis is used as the reference direction.

17. The X-ray facility of claim 13, wherein for ascertaining a relative torsion angle as an item of torsion information, recording the first X-ray image, recording the second X-ray image, and ascertaining are performed for ascertaining a distal roll angle for a distal end region and for ascertaining a proximal roll angle for a proximal end region; wherein after which the relative torsion angle is ascertained as an item of torsion information by forming a difference between the distal roll angle and the proximal roll angle.

18. The X-ray facility of claim 13, wherein the first projection geometry is automatically ascertained at least before carrying out recording the first X-ray image by evaluating at least one orientation image of the X-ray facility in at least one orientation geometry and/or ascertaining the reference direction in the first X-ray image, the second X-ray image, or the first X-ray image and the second X-ray image by at least one evaluation function.

19. The X-ray facility of claim 18, wherein in that for ascertaining the first projection geometry, at least one orientation landmark of the bone is detected by at least one trained one of the evaluation functions.

20. A non-transitory computer readable storage medium comprising a set of computer-readable instructions stored thereon for ascertaining an item of torsion information of a bone, of a patient, wherein an X-ray facility with adjustable projection geometry of a recording arrangement described by projection parameters is used, the X-ray facility comprising an X-ray source and an X-ray detector, the instructions which, when executed by at least one processor cause the processor to:

record a first X-ray image of an end region of the bone in a first projection geometry in which a torsion direction defined relative to at least one torsion landmark and used for ascertaining a roll angle lies in a first computing plane, which is formed by a focal point of the X-ray source and a reference direction that is determined in the first X-ray image by at least one reference landmark;

record a second X-ray image of the end region of the bone in a second projection geometry with a direction of projection deviating from the direction of projection of the first projection geometry and forming a second computing plane from the reference direction that is determined in the second X-ray image by the at least one reference landmark, and the focal point; and ascertain a three-dimensional course of the reference direction and the torsion direction from the first computing plane, the second computing plane, and the roll angle as a rotation of the torsion direction about the reference direction with respect to a comparison specification;

wherein the item of torsion information is ascertained from the roll angle.

* * * * *